US012605546B2

(12) United States Patent　　　　　(10) Patent No.:　US 12,605,546 B2
Van Furth　　　　　　　　　　　　　　(45) Date of Patent:　Apr. 21, 2026

(54) SYSTEMS AND METHODS FOR STIMULATING THE PITUITARY GLAND OR THE PITUITARY STALK

(71) Applicant: Academisch Ziekenhuis Leiden (H.O.D.N. LUMC), Leiden (NL)

(72) Inventor: Wouter R. Van Furth, Leiden (NL)

(73) Assignee: ACADEMISCH ZIEKENHUIS LEIDEN (H.O.D.N. LUMC), Leiden (NL)

( * ) Notice: Subject to any disclaimer, the term of this patent is extended or adjusted under 35 U.S.C. 154(b) by 291 days.

(21) Appl. No.: 18/276,221

(22) PCT Filed: Feb. 17, 2022

(86) PCT No.: PCT/NL2022/050082
　　§ 371 (c)(1),
　　(2) Date: Aug. 7, 2023

(87) PCT Pub. No.: WO2022/177427
　　PCT Pub. Date: Aug. 25, 2022

(65) Prior Publication Data
　　US 2024/0100339 A1　　Mar. 28, 2024

(30) Foreign Application Priority Data

Feb. 18, 2021　(NL) ..................................... 2027585

(51) Int. Cl.
　　*A61N 1/36*　　　(2006.01)
　　*A61N 1/05*　　　(2006.01)
(52) U.S. Cl.
　　CPC ....... *A61N 1/36071* (2013.01); *A61N 1/0529* (2013.01); *A61N 1/36121* (2013.01);
　　　(Continued)

(58) Field of Classification Search
　　CPC .............. A61N 1/36071; A61N 1/0529; A61N 1/36121; A61N 1/36171; A61N 1/36132
　　See application file for complete search history.

(56) References Cited

U.S. PATENT DOCUMENTS 7,440,806　B1 *　10/2008　Whitehurst ....... A61M 5/14276
　　　　　　　　　　　　　　　　　　　　　607/45
10,335,547　B2　　7/2019　Ward et al.
　　　　　　　　(Continued)

FOREIGN PATENT DOCUMENTS

EP　　　　3310429　B1　　12/2019
WO　　2020101493　A1　　5/2020

OTHER PUBLICATIONS

Takayanagi, Yuki, et al. "Activation of supraoptic oxytocin neurons by secretin facilitates social recognition." Biological Psychiatry 81(3): 243-251 (2017).

(Continued)

*Primary Examiner* — Joseph M Dietrich
(74) *Attorney, Agent, or Firm* — Viksnins Harris Padys Malen LLP

(57)　　　　ABSTRACT

The present invention relates to a system for use in the treatment or prevention of disease or symptoms thereof, the system comprising: at least one object, wherein the object is configured for being positioned in or adjacent to the pituitary gland or the pituitary stalk of a subject; and a device configured to generate at least one intermittent stimulating signal in the object, wherein the signal subsequently activates a release of biologically active agents.

6 Claims, 1 Drawing Sheet

100 Hz
100 µA 96 sec　　　　　　30 min　　　　　　96 sec

(52) U.S. Cl.
CPC ..... *A61N 1/36171* (2013.01); *A61N 1/36175* (2013.01); *A61N 1/36132* (2013.01); *A61N 1/36135* (2013.01)

(56) References Cited

U.S. PATENT DOCUMENTS

| | | |
|---|---|---|
| 2005/0065574 A1 | 3/2005 | Rezai |
| 2008/0255634 A1 | 10/2008 | Jaax et al. |
| 2012/0323214 A1 | 12/2012 | Shantha |
| 2020/0276441 A1 | 9/2020 | Van Furth et al. |

OTHER PUBLICATIONS

Augustine, Rachael A., et al. "Integrative neurohumoural regulation of oxytocin neurone activity in pregnancy and lactation." Journal of Neuroendocrinology 30(8): e12569 pp. 1-15 (2018).

Bicknell, R. J. "Optimizing release from peptide hormone secretory nerve terminals." Journal of Experimental Biology 139(1): 51-65 (1988).

Ludwig, Mike, and Javier Stem. "Multiple signalling modalities mediated by dendritic exocytosis of oxytocin and vasopressin." Philosophical Transactions of the Royal Society B: Biological Sciences 370(1672): 20140182 pp. 1-9 (2015).

Tobin, Vicky A., et al. "The involvement of voltage-operated calcium channels in somato-dendritic oxytocin release." PloS One 6(10): e25366 pp. 1-11 (2011).

Ludwig, Mike, and Gareth Leng. "Dendritic peptide release and peptide-dependent behaviours." Nature Reviews Neuroscience 7(2): 126-136 (2006).

Brown, Colin H., et al. "Physiological regulation of magnocellular neurosecretory cell activity: integration of intrinsic, local and afferent mechanisms." Journal of Neuroendocrinology 25(8): 678-710 (2013).

Leng, Gareth, Celine Caquineau, and Mike Ludwig. "Priming in oxytocin cells and in gonadotrophs." Neurochemical Research 33: 668-677 (2008).

Neumann, I. D. "Stimull and consequences of dendritic release of oxytocin within the brain." Biochemical Society Transactions 35(5): 1252-1257 (2007).

Johnson, Zachary V., and Larry J. Young. "Oxytocin and vasopressin neural networks: Implications for social behavioral diversity and translational neuroscience." Neuroscience & Biobehavioral Reviews 76: 87-98 (2017).

Ludwig, Mike, et al. "Intracellular calcium stores regulate activity-dependent neuropeptide release from dendrites." Nature 418(6893): 85-89 (2002).

Meyer-Lindenberg, Andreas, et al. "Oxytocin and vasopressin in the human brain: social neuropeptides for translational medicine." Nature Reviews Neuroscience 12(9): 524-538 (2011).

Leng, Gareth, and Mike Ludwig. "Neurotransmitters and peptides: whispered secrets and public announcements." The Journal of Physiology 586(23): 5625-5632 (2008).

Yanagida, Higashi, et al. "The pituitary inhibitory system: its role in pain perception." Brain Research 345(2): 356-361 (1985).

Yanagida, Hisashi, et al. "Electrical stimulation of the pituitary—its use in the treatment of cancer pain." The Pain Clinic 2(4): 225-228(1988).

Yanagida, Hisashi, et al. "Relief of cancer pain in man: alcohol-induced neuroadenolysis vs. electrical stimulation of the pituitary gland." Pain 19(2): 133-141 (1984).

Ohsu Brain Institute, "Understanding Pituitary Disorders", https://www.ohsu.edu/brain-institute/understanding-pituitary-disorders, 6 pages (2025).

\* cited by examiner

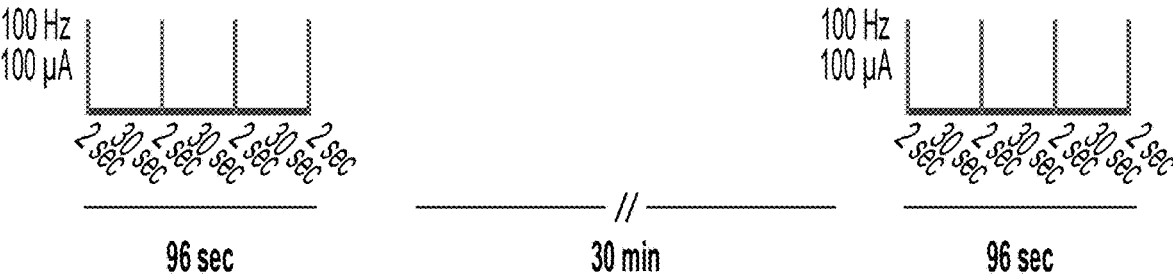

SYSTEMS AND METHODS FOR STIMULATING THE PITUITARY GLAND OR THE PITUITARY STALK

CROSS REFERENCE TO RELATED APPLICATIONS

This Application is a 35 U.S.C. § 371 National Phase Entry of International Patent Application No. PCT/NL2022/050082 filed Feb. 17, 2022, which designates the U.S. and claims benefit under 35 U.S.C. § 119(a) of NL Application No. 2027585 filed Feb. 18, 2021, the contents of which are incorporated herein in their entireties by reference.

FIELD OF THE INVENTION

The invention as disclosed in this application relates to systems and methods for use in the treatment or prevention of disease or symptoms thereof by stimulating the pituitary gland or the pituitary stalk of a subject.

BACKGROUND OF THE INVENTION

The human pituitary gland is a pea-sized endocrine gland located at the base of the brain. It protrudes from the bottom of the hypothalamus to which it is connected via the pituitary stalk, also known as the infundibulum. The pituitary gland is known to secrete hormones into the blood circulation that help control multiple physiological processes in the human body, including growth, blood pressure, aspects of pregnancy and childbirth, sex organ functions, thyroid glands, metabolism, breast milk production, control of reabsorption of water by the kidneys, regulation of water and osmolarity in the body, temperature regulation and pain relief.

The pituitary gland comprises three lobes, namely the anterior lobe, the posterior lobe, and the intermediate lobe joining the anterior and posterior lobes. The anterior lobe synthesizes and secretes hormones including growth hormone, adrenocorticotropic hormone, beta-endorphin, thyroid-stimulating hormone, luteinizing hormone, follicle-stimulating hormone and prolactin. These hormones are released from the anterior pituitary gland by signals originating from the hypothalamus. These signals comprise secreted hypothalamic hormones that travel to the anterior pituitary gland via a capillary system termed the hypothalamic-hypophysial portal system. The intermediate lobe is small in humans compared to other mammals and is known to synthesize and secrete melanocyte-stimulating hormone.

The posterior pituitary gland stores and secretes antidiuretic hormone (also known as vasopressin) and oxytocin. The posterior gland is an extension of the hypothalamus and the posterior gland hormones are synthesized by cell bodies (e.g. of magnocellular neurons) in the hypothalamus. Axons of (magnocellular) neurons of the supraoptic and paraventricular nuclei of the hypothalamus project down to the posterior pituitary gland via the pituitary stalk. Vasopressin and oxytocin can also be released from the dendrites of these magnocellular neurons or from dendrites of parvocellular neurons of the paraventricular nucleus, both of which are located in the hypothalamus, and thereby potentially act as neurotransmitters. Other neuropeptides are also produced by vasopressin or oxytocin magnocellular neurons, but the physiological importance of many of these are as of yet poorly characterized.

Using the pituitary gland as a target for treatment of disease or symptoms thereof has hitherto scarcely been described. However, a system and method for use in the treatment or prevention of cancer-associated pain by stimulating the pituitary gland of a subject is known and for example has been described in Yanagida et al. (1983). Yanagida et al. (1983) performed a clinical study comparing relief of cancer-associated pain in humans by alcohol-induced pituitary neuroadenolyis (NALP) versus electrical stimulation of the pituitary gland. An electrical stimulus consisting of a monophasic square wave of 0.3 msec duration and 4 mA was delivered at 20 c/sec for 5 min via an embedded bipolar electrode in the pituitary gland. While electrical stimulation was shown to have an effect they found that the duration of pain relief following NALP (59.65±68.72 days) was significantly longer compared with that recorded following electrical stimulation (2.97±2.58 days). The concept of this study using similar parameters (a monophasic square wave of 0.3 msec duration and 2 mA delivered at 50 Hz for 5 min) was repeated in Yanagida et al. (1988) by permanently implanting electrodes in three patients yielding long-lasting pain relief.

A disadvantage of Yanagida et al. (1983) and Yanagida et al. (1988) is that a relatively high-energy electrical stimulus was used to provide relief from oncological pain. In biological systems such a high-energy electrical stimulus can cause damage to the target area and surrounding areas resulting in possible undesirable side-effects. In addition, only oncological pain can be addressed by the methods and systems disclosed in Yanagida et al. (1983) and Yanagida et al. (1988) and not any other disease or symptom thereof. Both documents do not investigate the molecular working mechanisms responsible for the relief of pain by the electrical stimulation of the pituitary gland and therefore do not suggest any improvements to or alternative results from the treatment. Thus, there remains a need for improved methods and systems for use in the treatment or prevention of disease or symptoms thereof by stimulating the pituitary gland of a subject Accordingly, the invention of this application has as its goal to provide improved systems and methods for use in the treatment or prevention of disease or symptoms thereof by stimulating the pituitary gland or the pituitary stalk of a subject. These improved systems and methods preferably utilize a small amount of energy.

SUMMARY OF THE INVENTION

In view of the above discussion, the object of present invention is therefore to provide a system for use in the treatment or prevention of disease or symptoms thereof, the system comprising: at least one object, wherein the object is configured for being positioned in or adjacent to the pituitary gland or the pituitary stalk of a subject; and a device configured to generate at least one stimulating signal in the object, wherein the signal subsequently activates a release of biologically active agents.

It is a further object to provide a method for treating or preventing disease or symptoms thereof in a subject comprising the steps of:
  a. positioning at least one object in or adjacent to the pituitary gland or the pituitary stalk of a subject; and
  b. generating at least one stimulating signal in the object, wherein the signal subsequently activates a release of biologically active agents.

It is yet a further object to provide a system or method according to the invention wherein the at least one stimulating signal is an intermittent stimulating signal.

It is yet a further object to provide a system or method according to the invention, wherein the at least one object is an electrode, the at least one stimulating signal is an electrical signal, and the signal is a signal having a duration of up to 270 s.

In a further aspect, the subject of the invention is to provide the use of a system according to the invention for the treatment or prevention of disease or symptoms thereof, wherein the disease or symptoms thereof is pain.

Applicants have found that with the systems and methods according to the invention the goal has been achieved.

SHORT DESCRIPTION OF THE FIGURES

FIG. 1 shows a schematic representation of a stimulation session comprising two electrical intermittent stimulating signals interspaced by a resting period according to the example of the invention

DETAILED DESCRIPTION OF THE INVENTION

The pituitary gland is known to secrete hormones into the blood circulation that help control multiple physiological processes in the human body, including growth, blood pressure, aspects of pregnancy and childbirth, sex organ functions, thyroid glands, metabolism, breast milk production, control of reabsorption of water by the kidneys, regulation of water and osmolarity in the body, temperature regulation and pain relief. Synthetic, and often recombinant, pituitary gland-derived agents or pituitary gland-stimulating agents are directly or indirectly used in the treatment of various diseases, disorders or symptoms thereof. Non-limiting examples of these are desmopressin, an analogue of vasopressin, for use in the treatment of polyuric conditions including primary nocturnal enuresis, nocturia, and diabetes insipidus, carbetocin, an analogue of oxytocin, for use in the control of postpartum hemorrhage, sermorelin, an analogue of the amino-terminal segment of growth hormone, for use in the treatment of dwarfism, and nafarelin, an analogue of gonadotropin-releasing hormone that stimulates the release of luteinizing hormone and follicle-stimulating hormone, for use in the treatment of central precocious puberty and endometriosis.

A disadvantage with these agents is the need for a repeated and/or continuous administration to the subject. Another disadvantage is that these agents are administered to the circulation of a subject and cannot or cannot easily cross the blood-brain barrier. Therefore, their efficacy does not extend to the brain or the central nervous system and limits their use.

The present invention provides methods and systems for using a subject's own pituitary gland as a source of bioactive agents for the treatment or prevention of disease or symptoms thereof, thereby overcoming the need to administer, in time and in amount, exogenous pituitary-derived, -like, or -stimulating bioactive agents such as hormones, and providing an efficient administration route of bioactive agents to the brain or the central nervous system via the neurons connecting to the hypothalamus. A 'natural' hormone treatment using a subject's own supply and distribution means is thusly proposed herein.

The invention can be achieved by positioning an object in or adjacent to the pituitary gland or the pituitary stalk of a subject, after which a (intermittent) stimulating signal is generated in the object, wherein the signal subsequently activates a release of biologically active agents.

In some aspects more than one object is to be used in order to provide different means of stimulation at one or different locations in or near the pituitary gland or the pituitary stalk. The same holds true for the stimulating signal as different signals are better suited to stimulate different regions and/or cells of the pituitary gland or the pituitary stalk and/or are better suited to stimulate release of different biologically active agents or combinations thereof.

The present invention accordingly provides a system for use in the treatment or prevention of disease or symptoms thereof, the system comprising:

a. at least one object, wherein the object is configured for being positioned in or adjacent to the pituitary gland or the pituitary stalk of a subject; and
   b. a device configured to generate at least one stimulating signal in the object, wherein the signal subsequently activates a release of biologically active agents.

In addition, the present invention provides a method for treating or preventing disease or symptoms thereof in a subject comprising the steps of:

a. positioning at least one object in or adjacent to the pituitary gland or the pituitary stalk of a subject; and
   b. generating at least one stimulating signal in the object, wherein the signal subsequently activates a release of biologically active agents.

Biological systems, in particular tissues or cells, become less or even non-responsive after continuous stimulation, depending on the length of the stimulation and particular type of system or cell. An intermittent stimulation reduces this effect or even abolishes it. Therefore, for an effective method according to the invention it is necessary to provide an intermittent stimulating signal in the object for activation of release.

The present application provides a method or system according to the invention for treating or preventing disease or symptoms thereof in a subject, wherein the at least one stimulating signal is preferably an intermittent stimulating signal.

The release of bioactive agents can be a release from tissues or cells that act upon the pituitary gland, as is for example the case with neuroendocrine cells in the hypothalamus that project axons to the median eminence, at the base of the brain, where they can release bioactive agents in blood vessels that travel directly to the anterior pituitary gland via the hypophyseal portal system, or can be a release from the pituitary gland itself or tissues or cells that are in direct contact with the pituitary gland, such as the hypothalamus or cells thereof.

Accordingly, the release of biologically active agents according to invention is preferably a release from the median eminence, the pituitary gland or the hypothalamus of the subject. More preferably from the pituitary gland or the hypothalamus of the subject. More preferably from the posterior pituitary gland or the hypothalamus of the subject.

In order to provide a signal that is better directed and more efficient for activation it is necessary to place the object according to the invention in or adjacent to the pituitary gland or the pituitary stalk. Placing the object adjacent to the pituitary gland or the pituitary stalk can be achieved by penetrating the bony enclosure surrounding the pituitary gland; the sella turcica, after performing transsphenoidial surgery. Optionally, subsequently penetrating at least the meninges, including the dura mater, near the pituitary gland or the pituitary stalk enables positioning of the object in the respective structures. In some aspects of the invention a positioning of the object at a distance of the pituitary gland provides a sufficient signal for the treatment of prevention of disease or symptoms thereof.

The object can also be positioned nearer to the hypothalamic neurons of a patient to provide an alternative means for activation and subsequent release of biologically active agents. For example, continuing from the method for positioning the object adjacent to or into the pituitary gland or the pituitary stalk as described above the person skilled in the art can move the object further along the pituitary stalk towards the hypothalamus and position the object adjacent to the axons of the pituitary stalk or adjacent to a paraventricular nucleus or a supraoptic nucleus of the hypothalamus of a patient. Alternatively, the person skilled in the art can access these regions by penetrating the skull and then moving the object towards any of these regions.

"Adjacent" herein is understood to mean at a distance within 30 mm of, preferably at a distance within 20 or 10 mm of, more preferably at a distance within 5 or 2 mm of. Adjacent placing or positioning of a first object to a second object is intended to result in a functional interaction between the first and second object. For example, in the present invention the strength of a signal generated in a first object influences the degree of functional interaction between the first object and the second object. Therefore, in a biological setting there is a maximal distance that can be considered to be adjacent as the functional interaction becomes insufficient at a greater than maximal distance, while also potentially causing undesirable side-effects. An ideal adjacency would be on one hand as little a distance as possible as this would reduce the energy needed to produce a signal of sufficient strength for interaction between the first and second object. Therefore, a minimal adjacency would be as close to 0 as possible, or about 0. On the other hand, an ideal adjacency would also be at a distance that allows the first object to functionally interact or maximally interact with (the whole of) the second object. Different surrounding areas may be more or less amenable for allowing a functional interaction between (the whole of either or both of) the first and second object. For example, a first object placed at a greater distance to a second object in an area or tissue consisting mostly of water is more likely to more efficiently transfer an electrical signal to either a close or distant point of a second object than a first object placed at a closer distance to a second object in an area or tissue consisting mostly of fat, because of the difference in conductivity of both areas.

Accordingly, in an aspect, the object according to the invention is preferably configured for being positioned at a distance within 30 mm of or in the pituitary gland or the pituitary stalk, preferably at a distance within 20 or 10 mm of the pituitary gland or the pituitary stalk or more preferably within 5 or 2 mm of the pituitary gland or the pituitary stalk. The object according to the invention is preferably configured for being positioned at a distance within 30 mm of or in the posterior or anterior pituitary gland, preferably at a distance within 20 or 10 mm of the posterior or anterior pituitary gland or more preferably within 5 or 2 mm of the posterior or anterior pituitary gland.

Accordingly, in an aspect, the object according to the invention is preferably positioned at a distance within 30 mm of or in the pituitary gland or the pituitary stalk, preferably at a distance within 20 or 10 mm of the pituitary gland or the pituitary stalk or more preferably within 5 or 2 mm of the pituitary gland or the pituitary stalk. The object according to the invention is preferably positioned at a distance within 30 mm of or in the posterior or anterior pituitary gland, preferably at a distance within 20 or 10 mm of the posterior or anterior pituitary gland or more preferably within 5 or 2 mm of the posterior or anterior pituitary gland.

Alternatively, in another aspect, the object according to the invention is preferably positioned or configured to be positioned in or at a distance of from 0 to 30 mm from an axon of a pituitary stalk of a patient, in or at a distance of from 0 to 30 mm from a paraventricular nucleus of a hypothalamus of a patient or in or at a distance of from 0 to 30 mm from a supraoptic nucleus of the hypothalamus of a patient. Preferably, the distance is from 0 to 20 mm, from 0 to 10 mm or from 0 to 5 mm, more preferably from 0 to 2 mm.

The signal may be generated in the object by various means such as by electrical, magnetical, electromagnetical, sonic, photonic, physical, chemical or biological means.

Electrical means may for example be achieved by an electrode, magnetical means may for example be achieved by a magnet, potentially in combination with other objects comprising a metal, electromagnetical means may for example be achieved by a magnetic field generated by electricity optionally in combination with other objects comprising a metal, sonic means may for example be achieved by ultrasound, photonic means may for example be achieved by genetically modifying cells in the pituitary glands in such a way that they can become activated by light and providing a means of lighting, the physical means may for example be achieved by direct mechanical physical stimulation, the chemical means may for example be achieved by pharmaceutical compounds such as small molecule receptor agonists or antagonists, (modified) nucleic acids and the biological means may for example be achieved by (modified) antibodies, implanted cells.

Thus, in an aspect, the signal according to the invention may activate by electrical, magnetical, electromagnetical, sonic, photonic, physical, chemical or biological means, preferably by electrical means.

In a normal physiological setting the pituitary gland releases bioactive agents in response to signals originating from outside of the pituitary gland. These can for example be electrical neuronal signals or signals that act on receptors of cells of the pituitary gland. Such signals occur in a specific pattern in order to release an optimal amount and/or combination of bioactive agents that in turn act as an efficient physiological downstream signal originating from the pituitary gland. Thus, for the invention to achieve an optimal effect for the treatment or prevention of disease or symptoms thereof it is useful to mimic physiological signal patterns generated upstream of, or inside of, the pituitary gland.

In another aspect, the signal according to the invention comprises a biomimetic signal, which is a signal that is modulated such that it substantially resembles a normal physiological or biological signal pattern.

In biology, priming is a process by which biological systems, in particular cells, are 'primed' or activated by an initial signal after which the biological system or cell changes in order to be able to respond to subsequent similar signals in a stronger and/or faster way after receiving a similar subsequent signal. Thus, for the invention to achieve an optimal effect for the treatment or prevention of disease or symptoms thereof it is useful to generate a priming signal. A priming signal can be defined as a signal that is modulated such that a first signal activates less release of biologically active agents than a subsequent signal. The biologically active agents herein are meant to consist of essentially the same composition. Preferably the first signal releases no or a small amount of biologically active agents and the subsequent signal releases a large amount of biologically active agents compared to the amount released after the first signal.

A large amount is preferably at least 10, 100, 1000, 10000, 100000, 1000000 or 10000000 times more than a small amount.

In an aspect, the signal according to the invention is preferably modulated such that a first signal activates less release of biologically active agents than a subsequent signal.

Upon activation cells of the pituitary gland release biologically active agents. Such a release of biologically active agents from a cell comprises various elements including vesicles, vesicles comprising (poly)nucleotides such as nucleic acids, (poly)peptides, proteins or lipids, (poly)nucleotides such as nucleic acids, (poly)peptides, proteins or lipids that can all have a signaling function of their own. For the invention to be more useful for the treatment or prevention of disease or symptoms thereof the use of known and well-characterized factors that are released from the pituitary gland or hypothalamus and the ability to generate a signal that releases such factors is preferred.

In another aspect, the biologically active agents according to the invention are preferably peptides, more preferably hormones, such as for example oxytocin.

Yanagida et al. (1983), Yanagida et al. (1988) and Fujita et al. (1984) disclose positive effects after stimulating the pituitary gland by an electrical signal via an electrode and by using a continuous signal with a duration of at least 5 min. Thus, a disclosed method of activating the pituitary gland is by using an electrical signal via an electrode.

In another aspect, the at least one object according to the invention preferably is an electrode, the at least one stimulating signal preferably is an electrical signal.

Yanagida et al. (1983), Yanagida et al. (1988) and Fujita et al. (1984) disclose the use of a long-lasting, and very strong electrical signal. Long-lasting, continuous or very strong signals acting on biological systems, in particular cells, have the effect that the cells can become desensitized to the signal and thus react in a strongly reduced manner to the signal or even become unresponsive. This serves to limit or restrain a cell's responses to stimuli.

Desensitization can be biochemically explained by the fact that a receptor of a cell decreases its response to an agonist, thereby reducing or abolishing the normal translation of the receptor signal. Desensitization of postsynaptic receptors can also occur by for example decreasing their response to the same neurotransmitter stimulus. Thus, release of biologically active agents that are of use in the treatment or prevention of disease or symptoms thereof according to the invention can be hindered by long-lasting, continuous and/or very strong signals.

Accordingly, in another aspect the signal according to the invention is preferably a signal having a duration of up to 30 min, 20 min, 10 min, 5 min, more preferably up to 270 s, of up to 240 s, 210 s, 180 s, 150 s, 120 s, 90 s, 80 s, 70 s, 60 s, 50 s, 40 s, 35 s, 30 s, 25 s, 20 s, 19 s, 18 s, 17 s, 16 s, 15 s, 14 s, 13 s, 12 s, 11 s, 10 s, 9.5 s, 9.0 s, 8.5 s, 8.0 s, 7.5 s, 7.0 s, 6.5 s, 6.0 s, 5.5 s, 5.0 s, 4.5 s, 4.0 s, 3.5 s, 3.0 s, 2.5 s, 2.0 s, 1.5 s, 1.0 s or 0.5 s.

In yet another aspect the signal according to the invention is preferably a signal having a duration of from 0.5 to 10 s, of from 0.5 to 9.0 s, of from 0.5 to 8.0 s, of from 0.5 to 7.0 s, of from 0.5 to 6.0 s, of from 0.5 to 5.0 s, of from 0.5 to 4.0 s, of from 0.5 to 3.0 s, of from 0.5 to 2.0 s, of from 0.5 to 1.0 s, of from 1.0 to 10 s, of from 1.0 to 9.0 s, of from 1.0 to 8.0 s, of from 1.0 to 7.0 s, of from 1.0 to 6.0 s, of from 1.0 to 5.0 s, of from 1.0 to 4.0 s, of from 1.0 to 3.0 s, of from 1.0 to 2.0 s, of from 2.0 to 10 s, of from 2.0 to 9.0 s, of from 2.0 to 8.0 s, of from 2.0 to 7.0 s, of from 2.0 to 6.0 s, of from 2.0 to 5.0 s, of from 2.0 to 4.0 s, of from 2.0 to 3.0 s, of from 3.0 to 10 s, of from 3.0 to 9.0 s, of from 3.0 to 8.0 s, of from 3.0 to 7.0 s, of from 3.0 to 6.0 s, of from 3.0 to 5.0 s, of from 3.0 to 4.0 s, of from 4.0 to 10 s, of from 4.0 to 9.0 s, of from 4.0 to 8.0 s, of from 4.0 to 7.0 s, of from 4.0 to 6.0 s, of from 4.0 to 5.0 s, of from 5.0 to 10 s, of from 5.0 to 9.0 s, of from 5.0 to 8.0 s, of from 5.0 to 7.0 s, of from 5.0 to 6.0 s, of from 1.5 to 5.0 s, of from 1.5 to 4.0 s, of from 1.5 to 3.0 s, of from 1.5 to 2.5 s, of from 1.5 to 2.0 s, of from 2.5 to 5.0 s, of from 2.5 to 4.0 s or of from 2.5 to 3.0 s, more preferably of from 1.5 to 2.5 s.

Applicants have found that generating an intermittent signal near the pituitary gland or the pituitary stalk of a subject via an object causes a release of biologically active agents from the pituitary gland or hypothalamus of the subject in such a way that specific combinations of bioactive agents are released from the pituitary gland or hypothalamus of the subject for treating or preventing disease or symptoms thereof in a subject. Adjusting the intermittent signal by its means, composition and/or pattern can accordingly be done in a bespoke manner with regard to a specifically to be treated disease or symptoms thereof.

Modulating the stimulating signal by generating multiple subsequent signals with periods of no signal in between the subsequent signals has the advantage of potentially priming and preventing desensitization. In addition, a bespoke pattern can be generated in this manner with regard to a specifically to be treated disease or symptoms thereof.

In an aspect, a signal according to the invention preferably comprises a set of at least two subsequent signals, wherein the duration between the end of a signal and the start of a subsequent signal is of from 1 to 60 s.

The at least two subsequent signals are preferably at least three, at least four, at least five, at least six, at least seven, at least eight, at least nine or at least ten, more preferably at least four. The duration between the end of a signal and the start of a subsequent signal is preferably of from 1 to 60 s, of from 10 to 60 s, of from 20 to 60 s, of from 30 to 60 s, of from to 60 s, of from 50 to 60 s, of from 1 to 40 s, of from 10 to 40 s, of from 20 to 40 s, of from to 40 s, of from 1 to 50 s, of from 10 to 50 s, of from 20 to 50 s, of from 30 to 50 s, of from 40 to 50 s, of from 1 to 30 s, of from 10 to 30 s, of from 20 to 30 s, of from 1 to 20 s, of from to 20 s or of from 1 to 10 s, more preferably of from 10 to 50 s or of from 20 to 40 s.

For some treatments it is advantageous to increase the rest, recovery or interval period between signals or sets of signals. The preferred period depends on the to be treated disease or symptoms thereof.

In another aspect the signal or the set of subsequent signals according to the invention preferably are repeated at least one time with an interval of from 1 min to 72 h.

The signal or the set of subsequent signals preferably are repeated at least one time with an interval of from 1 min to 72 h, preferably of from 1 min to 24 h, of from 1 to 180 min, of from 1 to 120 min, of from 1 to 60 min, of from 1 to 50 min, of from 1 to 40 min, of from 1 to 30 min, of from 1 to 20 min, of from 1 to 10 min, of from 1 to 5 min, of from 10 to 180 min, of from 10 to 120 min, of from 10 to 60 min, of from 10 to 50 min, of from 10 to 40 min, of from to 30 min, of from 10 to 20 min, of from 20 to 180 min, of from 20 to 120 min, of from 20 to 60 min, of from 20 to 50 min, of from 20 to 40 min, of from 20 to 30 min, of from 30 to 180 min, of from 30 to 120 min, of from 30 to 60 min, of from 30 to 50 min, of from 30 to 40 min, of from 40 to 180 min, of from 40 to 120 min, of from 40 to 60 min, of from 40 to 50 min, of from 60 to 180 min, of from 60 to 120 min, of from 120 to 180 min, of from 24 h to 36 h, of from 24 h to 48 h, of from 24 h to 72 h, of from 36 h to 48 h, of from 36 h to 72 h, of from 48 h to 72 h, of from 3 to 24 h, of from 4 to 24 h, of from 6 to 24 h, of from 8 to 24 h, of from 12 to 24 h, of from 3 to 12 h, of from 4 to 12 h, of from 6 to 12 h, of from 8 to 12 h, of from 3 to 8 h, of from 4 to 8 h, of from 6 to 8 h, of from 3 to 6 h, of from 4 to 6 h, or of from 3 to 4 h, more preferably of from 10 to 50 min or of from 20 to 40 min.

Modulating the signal by adjusting the frequency can result in the release of different compositions of bioactive agents depending on the frequency and thus can be used to produce a bespoke signal with regard to a specifically to be treated disease or symptoms thereof. In for example FIG. 1 of Bicknell (1988), it is disclosed that a different amount and ratio of oxytocin and vasopressin is released from neurohypophyses in vitro at different frequencies.

A signal according to the invention is preferably a signal having a frequency of at least 10 Hz. The signal preferably has a frequency of at least 20 Hz, of at least 30 Hz, of at least 40 Hz, of at least 50 Hz, of at least 60 Hz, of at least 70 Hz, of at least 80 Hz, of at least 90 Hz, of at least 100 Hz, of from 10 to 500 Hz, of from 20 to 500 Hz, of from 30 to 500 Hz, of from to 500 Hz, of from 50 to 500 Hz, of from 100 to 500 Hz, of from 10 to 400 Hz, of from 20 to 400 Hz, of from 30 to 400 Hz, of from 40 to 400 Hz, of from 50 to 400 Hz, of from 100 to 400 Hz, of from 10 to 300 Hz, of from 20 to 300 Hz, of from 30 to 300 Hz, of from 40 to 300 Hz, of from 50 to 300 Hz, of from 100 to 300 Hz, of from 10 to 200 Hz, of from 20 to 200 Hz, of from 30 to 200 Hz, of from 40 to 200 Hz, of from 50 to 200 Hz, of from 100 to 200 Hz, of from 10 to 150 Hz, of from 20 to 150 Hz, of from 30 to 150 Hz, of from 40 to 150 Hz, of from 50 to 150 Hz, of from 60 to 150 Hz, of from 70 to 150 Hz, of from 80 to 150 Hz, of from 90 to 150 Hz, of from 100 to 150 Hz, of from 10 to 125 Hz, of from 20 to 125 Hz, of from 30 to 125 Hz, of from 40 to 125 Hz, of from 50 to 125 Hz, of from 60 to 125 Hz, of from 70 to 125 Hz, of from 80 to 125 Hz, of from 90 to 125 Hz, of from 100 to 125 Hz, of from 10 to 110 Hz, of from 20 to 110 Hz, of from 30 to 110 Hz, of from 40 to 110 Hz, of from 50 to 110 Hz, of from 60 to 110 Hz, of from 70 to 110 Hz, of from 80 to 110 Hz, of from 90 to 110 Hz, of from 100 to 110 Hz, of from 10 to 100 Hz, of from 20 to 100 Hz, of from 30 to 100 Hz, of from 40 to 100 Hz, of from 50 to 100 Hz, of from 60 to 100 Hz, of from 70 to 100 Hz, of from 80 to 100 Hz or of from 90 to 100 Hz, more preferably of from 90 to 110 Hz.

The frequency of a signal can be irregular with regard to the fact that the positive half of a signal cycle can have a different duration than the negative half. This occurs for example with signals having a constant period, but are of a rectangular waveform or of an asymmetrical pulse waveform. The positive half of the signal cycle has a certain duration, which is termed the pulse width. The signal can thus be modulated with regard to the pulse width in order to generate a bespoke pattern for a specifically to be treated disease or symptoms thereof.

An aspect is a signal according to the invention preferably having a pulse width of from 10 μs to 1 ms, of from 10 to 800 μs, of from 10 to 500 μs, of from 10 to 300 μs, of from 10 to 100 μs, of from 30 μs to 1 ms, of from 30 to 800 μs, of from 30 to 500 μs, of from 30 to 300 μs, of from 30 to 100 μs, of from 60 μs to 1 ms, of from 60 to 800 μs, of from 60 to 500 μs, of from 60 to 300 μs, of from 60 to 100 μs, of from 100 μs to 1 ms, of from 100 to 800 μs, of from 100 to 500 μs, of from 100 to 300 μs, of from 300 μs to 1 ms, of from 300 to 800 μs, of from 300 to 500 μs, of from 500 μs to 1 ms or of from 500 to 800 μs, more preferably of from 60 to 300 μs.

The strength of a signal can be used to modulate the release of bioactive agents. For electrical, magnetic, electromagnetic, photonic or sonic signals the strength can be modulated by varying the amplitude of the signal.

Accordingly, a signal according to the invention is preferably a signal having an amplitude of from 100 μA to 8 mA, of from 100 μA to 6 mA, of from 100 μA to 4 mA, of from 100 μA to 2 mA, of from 100 μA to 1 mA, of from 100 μA to 500 μA, of from 100 μA to 250 μA, of from 250 μA to 8 mA, of from 250 μA to 6 mA, of from 250 μA to 4 mA, of from 250 μA to 2 mA, of from 250 μA to 1 mA, of from 250 μA to 500 μA, of from 500 μA to 8 mA, of from 500 μA to 6 mA, of from 500 μA to 4 mA, of from 500 μA to 2 mA, of from 500 μA to 1 mA, of from 1 to 8 mA, of from 1 to 6 mA, of form 1 to 4 mA, of from 1 to 2 mA, of from 2 to 8 mA, of from 2 to 6 mA, of form 2 to 4 mA, of from 4 to 8 mA or of from 4 to 6 mA, more preferably of from 100 μA to 4 mA.

A signal can consist of one or more phases. The simplest signal is the monophasic or single phase signal. An electrical monophasic signal has a unidirectional waveform which is always positive or negative. Examples of unidirectional waveforms are square-wave timing signals, clock pulses and trigger pulses. A biphasic signal consists of two different phases that can be symmetrical or asymmetrical. An electrical biphasic signal is usually a bidirectional wave with one positive phase and one negative phase and is then also termed an alternating wave. A common example of a bidirectional waveform is the sine wave. A polyphasic signal consists or more than one phase, usually at least three.

As either a constant negative, a constant positive or an alternating (biphasic) electrical signal has a different effect on the bioactive agents released the signal can be modulated with regard to the phase of the signal in order to generate a bespoke pattern for a specifically to be treated disease or symptoms thereof.

Another aspect of the invention is a signal according to the invention which is preferably monophasic, biphasic or polyphasic, more preferably monophasic.

An electrical signal can be generated via a monopolar or a bipolar configuration. Monopolar configuration can be understood to mean that a stimulating electrode is positioned in or adjacent to the target area and that a return or ground electrode is positioned at a position wherein a stimulating current generated by the stimulating electrode passes through the target area and one or more other areas before reaching the return or ground electrode. Monopolar stimulation can be understood to mean a signal generated in a monopolar configuration. Bipolar configuration can be understood to mean that a stimulating electrode is positioned in or adjacent to the target area and that a return electrode is also positioned in or adjacent to the target area such that a stimulating current generated by the stimulating electrode passes only through the target area before reaching the return electrode. Bipolar stimulation can be understood to mean a signal generated in a monopolar configuration. The different configurations result in different stimulation regions, required intensities and potential side effects.

Accordingly, an aspect is a signal according to the invention which is preferably generated by monopolar stimulation or bipolar stimulation, more preferably monopolar stimulation.

In addition, a system according to the invention comprises at least two leads comprising at least one electrode each or at least one lead comprising at least two electrodes.

A system according to the invention, wherein the at least one stimulating signal is an electrical signal can comprise various components such as a current source, preferably connected to the at least one object, which comprises an electrode, and a pulse or function generator. A current source herein is understood to mean an electronic circuit configured to deliver or absorb an electric current. An ideal current source generates a current that is independent of the voltage changes across it. A voltage source may also be used, preferably connected to the at least one object, which is an electrode. A voltage source herein is understood to mean a two-terminal device which is configured to maintain a fixed voltage. A pulse generator herein is understood to mean an electronic system configured to generate rectangular pulses. A function generator herein is understood to mean an electronic system configured to generate various types of electrical waveforms over various frequencies. The electronic system may comprise software.

Thus, a system according to the invention preferably comprises a current source or a voltage source. Preferably, the current source or voltage source is connected to the at least one object, which is an electrode. A system according to the invention preferably comprises a pulse generator or a function generator.

In addition, a system according to the invention preferably comprises a controller configured to control operation of the device. Yet further, the system advantageously comprise any lead or antenna required to transfer the signal, and where needed electrical power.

An aspect of the invention is a system according to the invention, wherein the system further comprises a current source connected to the at least one electrode, a controller configured to control operation of the device and a pulse or function generator.

For an effective treatment according to the invention it is useful to determine the release of the bioactive agents and their effect on the subject, the effect being determined based on either the physiological or the pathological status of the subject.

An aspect preferably comprises a system or method according to the invention comprising a means for determining the release of bioactive agents in the subject. The release of bioactive agents is preferably determined in the brain or in the systemic circulation of the subject.

The release of bioactive agents can be determined by methods, systems and means known in the art such as by obtaining a fluid sample or biopsy from the subject and determining the amount of bioactive agents via standard biological assays that make use of for example any or all of enzyme-linked immunosorbent assay (ELISA), high performance liquid chromatography (HPLC) or mass spectrometry.

The release of bioactive agents can also be determined indirectly based on the physiological or the pathological status of the subject.

Therefore, an aspect preferably comprises a system or method according to the invention comprising a means for determining a physiological or pathological status of the subject, wherein the status is preferably a cardiovascular, cardiac, vascular, pulmonary, blood oxygen or pain status, wherein the pain status is reported by the subject.

The status can be determined by methods, systems and means known in the art such as by standard clinical methods, systems and means that make use of for example any or all of electrocardiogram such as exercise echocardiogram, transthoracic echocardiogram or transesophageal echocardiogram, electroencephalography, positron emission tomography, computed tomography, positron emission tomography-computed tomography, single-photon emission computed tomography, magnetic resonance imaging, functional magnetic resonance imaging, scintigraphy, thallium scan, myocardial perfusion scan, angiography, radiography, bronchoscopy, plethysmography, pulmonary function tests, spirometry, near-infrared spectroscopy or pulse oximetry.

The release of bioactive agents can also be determined based on the electrical activity of the pituitary gland or hypothalamus. This can for example be assessed via an electrode implanted in or adjacent to the pituitary gland or hypothalamus, preferably the same electrode that is used to transfer the stimulating signal.

Thus, an aspect preferably comprises a system or method according to the invention comprising a means for determining the electrical activity of the pituitary gland or the hypothalamus.

The determination of the release of bioactive agents and/or the status of the subject can then be used to detect the efficacy of the treatment of or the prevention of the disease or symptoms thereof according to the invention; such a release or alteration in the status can be determined by the means described above.

Accordingly, an aspect preferably comprises a system or method according to the invention comprising a means for detecting the efficacy of the treatment of or the prevention of the disease or symptoms thereof.

In contrast, the status of the subject can also be used to detect the presence or onset of a disease or symptoms thereof. This is particularly useful when the subject is undergoing treatment according to the invention in order to initiate or adjust a release of bioactive agents according to the invention, thereby treating or preventing the disease or symptoms thereof.

An aspect preferably comprises a system or method according to the invention comprising a means for detecting the presence or onset of a disease or symptoms thereof.

The release of bioactive agents can change during treatment according to the invention and may vary from individual subject to individual subject. In order to adapt the stimulation signal accordingly and to achieve an effective treatment according to the invention it is useful to receive a feedback signal related to the release of bioactive agents such as a signal related to the activity of the pituitary gland or hypothalamus. An example of a means for determining that provides feedback that can be used to alter the signal would be an electrode that measures the electrical activity of the pituitary gland or hypothalamus and is connected to an output device that displays the electrical activity.

Therefore, an aspect of the invention preferably comprises a system or method according to the invention comprising a means for determining that provides feedback that can be used to alter the signal.

Applicants disclose herein that the methods or systems according to the invention can be used for the treatment or prevention of disease or symptoms thereof, preferably for the treatment or prevention of pain.

An aspect of the invention thus preferably comprises a system for use in, or method of treatment for, according to the invention, the treatment or prevention of pain, more preferably wherein the pain is oncological pain or inflammatory pain.

Another aspect of the invention is the use of a system according to the invention for the treatment or prevention of disease or symptoms thereof, wherein the disease or symptoms thereof is preferably pain, more preferably wherein the pain is oncological pain or inflammatory pain.

A further aspect of the invention relates to the use of a computing system in which embodiments of the above device and method may be implemented. Components of the computing system may include, but are not limited to, a computing device having a processing unit, a system memory, and a system bus that couples various system components including the system memory to the processing unit. The system bus may be any of several types of bus structures including a memory bus or memory controller, a peripheral bus, and a local bus using any of a variety of bus architectures.

The computing system may typically include a variety of computer-readable media products. Computer-readable media may include any media that can be accessed by the computing device and include both volatile and nonvolatile media, removable and non-removable media. By way of example, and not of limitation, computer-readable media may include computer storage media. By way of further example, and not of limitation, computer-readable media may include a communication medium. Computer storage media may include volatile and nonvolatile, removable and non-removable media implemented in any method or technology for storage of information such as computer-readable instructions, data structures, program modules, or other data. Computer storage media include, but are not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device. In a further embodiment, a computer storage medium may include a group of computer storage media devices. In another embodiment, a computer storage medium may include an information store. In another embodiment, an information store may include a quantum memory, a photonic quantum memory, or atomic quantum memory. Combinations of any of the above may also be included within the scope of computer-readable media. Communication media may typically embody computer-readable instructions, data structures, program modules, or other data in a modulated data signal such as a carrier wave or other transport mechanism and include any information delivery media. By way of example, and not limitation, communication media include wired media, such as a wired network and a direct-wired connection, and wireless media such as acoustic, RF, optical, and infrared media.

DETAILED DESCRIPTION OF THE FIGURE

The invention will now be discussed with reference to the FIG. 1, which shows a preferred exemplary embodiment of the subject invention.

FIG. 1 shows a schematic representation of a stimulation session comprising two electrical intermittent stimulating signals interspaced by a resting period according to the example of the invention. An intermittent signal of monophasic square waved pulses with the following characteristics is generated: a pulse amplitude of 100 µA, a pulse width of 300 µs, a frequency of 100 Hz and a duration of 2 s, which is followed by no signal for 30 s. This is repeated 3 times.

The aforementioned set of signals is repeated after 30 min of no signal resulting in one stimulation session.

EXAMPLE

The following example serves to illustrate the invention and is non-limitative.

Oxytocin is considered to have a modulatory effect on pain processing as is exemplified in various animal studies (Boll et al., 2018). However, studies on the role of oxytocin in pain perception in humans are not as abundant and have inconsistent results (Boll et al., 2018). Therefore, no definitive conclusions about the effect of oxytocin on pain in humans can be drawn.

A subject diagnosed with cancer and suffering from a 6-month history of cancer-associated pain is anesthetized. Via standard transsphenoidial surgery techniques and entry via the nostril of the subject a small portion of the nasal septum is removed. Next, the front wall of the sphenoid sinus is opened to access the sella. A hole is made in the bone of the sella after which the dura is identified. A thin, flat surface electrode is, epidurally, placed between the sella turcica and pituitary dura, with one or multiple contact points adjacent to the pituitary gland. At least one contact point is placed adjacent to the posterior lobe of the pituitary gland. In addition, a ground electrode is placed in the sphenoid sinus or nasal cavity at a distance from the surface electrode. The electronic leads are guided through the nostril and covered with mucosa. The electrodes are secured via attachment to the local bone.

The surface electrode is attached outside the body of the subject to a current source and a pulse generator. A controller automatically operates the generation of an electrical signal via the electrode, current source and pulse generator at set timings and intervals. The timings and intervals can be adjusted based on feedback received from the subject regarding self-reported efficacy of the treatment. This adjustment can be done via software that directs the controller.

After surgery a recurring signal stimulates release of bioactive agents in the subject via the implanted electrode. The signal is configured to cause an optimal release of oxytocin into the brain by the dendrites of the oxytocin magnocellular neurons located in the supraoptic and paraventricular nuclei of the hypothalamus, the axons of which project into the posterior pituitary gland, while minimizing the release of vasopressin. This is achieved by imitating the electrophysiological difference between the oxytocin-releasing and vasopressin-releasing neurons (Armstrong et al., 2010). Optimization of oxytocin release involves utilizing a property of frequency facilitation and minimizing a process of fatigue in the release mechanism.

An optimized electrical signal used in the treatment of pain of the subject of this example is an intermittent signal of monophasic square waved pulses with the following characteristics: a pulse amplitude of 100 µA, a pulse width of 300 µs, a frequency of 100 Hz and a duration of 2 s, which is followed by no signal for 30 s. This is repeated 3 to 4 times. The aforementioned set of signals is repeated after 30 min of no signal resulting in one stimulation session. Pulse amplitude can be gradually increased up to a maximum pulse amplitude of 4 mA until the patient has side-effects, or clinical benefit.

The degree of pain is evaluated on a 0-10 numerical pain rating scale.

Thus, via electrical stimulation of the pituitary gland oxytocin levels in the brain are increased. Prolonged relief of (oncological) pain is achieved in the above example.

REFERENCES

Armstrong W. E., Wang L., Li C., Teruyama R. (2010). Performance, properties, and plasticity of identified oxytocin and vasopressin neurones in vitro. J. NEUROENDOCR. 22(5):330-342. doi: 10.1111/j.1365-2826.2010.01989.x Bicknell R. J. (1988). Optimizing release from peptide hormone secretory nerve terminals. J. EXP. BIOL. 139: 51-65.

Boll S., Almeida de Minas A. C., Raftogianni A., Herpertz S. C., Grinevich V. (2018). Oxytocin and Pain Perception: From Animal Models to Human Research. NEUROSCIENCE. 387: 149-161. doi: 10.1016/j.neuroscience.2017.09.041

Fujita T., Kitani Y., Takeda, F. (1984). Mechanism of pain relief by nalp—a comparison of electric stimulation and nalp. PAIN. 18. S117. doi: 10.1016/0304-3959(84)90302-6

Yanagida H., Corssen G., Trouwborst A., Erdmann W. (1984). Relief of cancer pain in man: alcohol-induced neuroadenolysis vs. electrical stimulation of the pituitary gland. PAIN. 19(2): 133-141. doi: 10.1016/0304-3959(84)90833-9

Yanagida H., Suwa K., Trouwborst A., Erdmann W., Corssen G. (1988). Electrical stimulation of the pituitary—its use in the treatment of cancer pain. THE PAIN CLINIC. 2(4): 225-228.

The invention claimed is:

1. A method for treating pain in a subject comprising the steps of:

a) positioning at least one object epidurally between the sella *turcica* and the pituitary dura at a distance within 30 mm of the pituitary gland or the pituitary stalk of a subject, preferably the posterior pituitary gland; and b) generating at least one stimulating signal in the object, wherein the signal subsequently activates a release of biologically active agents from the pituitary gland or hypothalamus of the subject by electrical means, wherein the at least one object is an electrode, and the at least one stimulating signal is an electrical signal.

2. The method according to claim 1, wherein in step b) the signal comprises a set of at least two, preferably four, subsequent electrical signals in at least one electrode, wherein the duration between the end of a signal and the start of a subsequent signal is of from 10 to 50 s, the method further comprising:

c) repeating the signal or the set of subsequent signals at least one time with an interval of from 10 to 50 min, preferably of from 20 to 40 min.

3. The method according to claim 1, wherein the signal in step b) is a signal having a frequency of at least 10 Hz, and wherein the signal has a duration of from 0.5 to 10 s, an amplitude of from 100 μA to 8 mA, and a pulse width of from 10 to 500 μs.

4. The method according to claim 1, for the treatment of oncological pain or inflammatory pain.

5. The method according to claim 1, wherein the at least one stimulating signal comprises an intermittent stimulating signal, and wherein the at least one stimulating signal has a duration of up to 270 s.

6. The method according to claim 1, wherein the biologically active agents comprises at least one of: peptides and hormones.

* * * * *